United States Patent [19]

Vogler et al.

[11] Patent Number: 5,246,666
[45] Date of Patent: Sep. 21, 1993

[54] ADDITIVE HAVING DUAL SURFACE CHEMISTRY FOR BLOOD COLLECTION CONTAINER AND ASSEMBLY CONTAINING SAME

[75] Inventors: Erwin A. Vogler, Newhill; Garry R. Harper, Raleigh, both of N.C.

[73] Assignee: Becton, Dickinson and Company, Franklin Lakes, N.J.

[21] Appl. No.: 880,396

[22] Filed: May 8, 1992

[51] Int. Cl.$^5$ .......................................... G01N 33/00
[52] U.S. Cl. .................................... 422/73; 422/101; 422/102; 436/69; 436/177; 435/2; 428/405; 128/760; 210/504; 210/506
[58] Field of Search .................... 422/73, 101, 102, 57; 435/2; 436/69, 177; 210/504, 506; 128/760, 771; 428/405

[56] References Cited

U.S. PATENT DOCUMENTS

| | | | |
|---|---|---|---|
| 4,131,549 | 12/1978 | Ferrara | 128/764 X |
| 4,656,083 | 4/1987 | Hoffman et al. | 128/DIG. 22 X |
| 4,711,820 | 12/1987 | Arkles et al. | 428/429 |
| 4,770,779 | 9/1988 | Ichikawa et al. | 422/102 X |
| 4,886,071 | 12/1989 | Mehl et al. | 128/760 |
| 4,957,582 | 9/1990 | Columbus | 128/760 X |
| 5,019,243 | 5/1991 | McEwen et al. | 422/102 X |
| 5,045,201 | 9/1991 | Dubois et al. | 210/504 X |

Primary Examiner—James C. Housel
Assistant Examiner—Maureen M. Wallenhorst
Attorney, Agent, or Firm—Richard E. Brown

[57] ABSTRACT

An additive for a blood collection tube has a wettable surface region and a nonwettable surface region. When a blood sample comes into contact with the wettable surface region, the clotting cascade is initiated. Clot material adheres to the nonwettable surface region. The additive thereby becomes part of the clot and, on centrifugation, becomes part of the pellet and is removed from the serum layer. The invention includes a blood collection tube having the additive therein. The tube may be evacuated and have an open end covered with a septum.

21 Claims, 2 Drawing Sheets

ADDITIVE HAVING DUAL SURFACE CHEMISTRY FOR BLOOD COLLECTION CONTAINER AND ASSEMBLY CONTAINING SAME

BACKGROUND OF THE INVENTION

1. Field of the Invention

This invention relates to blood sample collection and more particularly relates to an additive for a blood collection container which facilitates separation of the sample into its components.

2. Background

Blood samples are routinely taken in evacuated glass tubes. Plastic tubes also have been proposed for blood collection. One end of a double-ended needle is inserted into a patient's vein. The other end of the needle then punctures a septum covering the open end of the collection tube so that the vacuum in the tube draws the blood sample through the needle into the tube. Using this technique a plurality of blood samples can be taken using a single needle puncture of the skin.

Prior to analysis, blood samples are routinely clotted and centrifuged. The clotting process is slow, often taking 30 minutes or more to complete. This length of time is unacceptable for many routine blood analysis operations, and as a result clotting activators are often added. Typical activators are diatomaceous earth and particles of inorganic silicates, or biochemicals such as ellagic acid and thromboplastin. In one line of commercial blood collection tubes, a coating of silicate particles in polyvinylpyrrolidone (PVP) is affixed to the inside wall of the tube. When blood enters the tube, it dissolves the PVP releasing the silicate particles to initiate clotting. These finely divided activator particles may not pellet completely with the clot and may thus remain in the serum layer, a detriment for certain blood analyses, and may foul automatic blood analysis instruments.

There is need in the art of blood collection for a blood clot activator that enhances the rate of blood coagulation but which does not remain within the serum layer on centrifugation, thus avoiding potential interference with clinical tests.

SUMMARY OF THE INVENTION

An additive for a blood collection container has a plurality of surface regions which exhibit different surface chemistries.

A first surface region of the additive is a substantially wettable surface which activates the clotting cascade. A second surface region of the additive is a substantially nonwettable surface which absorbs blood proteins and adheres fibrin as it is formed. The additive may be a glass particle in which the native wettable glass surface is the first region, and a surface region treated to be nonwettable serves as the second region.

The preferred additive is a particle of a substantially nonwettable polymer in which the native polymeric surface serves as the second region and a surface region treated to be wettable serves as the first region. The most preferred additive is a piece of polystyrene or polypropylene film which has been treated on one side with an oxidative plasma to be wettable.

When absorbed in the clot, the additive of the invention causes the clot to pack tightly into a smaller clot volume than occurs with conventional clot activators so that a higher volume of serum is obtained from a given quantity of whole blood sample.

A second aspect of the invention is a blood collection assembly. The assembly may contain a blood collection tube having the additive of the invention therein. The preferred assembly is an evacuated plastic tube having a closed end and an open end covered by a septum.

Thus, the invention provides a blood tube additive that performs the dual functions of first activating the clotting mechanism and second adhering to clotted material. When the additive adheres to clotted material, it becomes part of the clot, and on conventional centrifugation, is removed from serum in the pellet. The serum is free of any foreign material added to promote clotting and is ready for blood analysis. The size, shape and surface-to volume ratio of the additive relative to the blood sample is easily optimized so that samples of any size can be quickly processed with minimal effect on any blood components.

DETAILED DESCRIPTION

Figure 1:
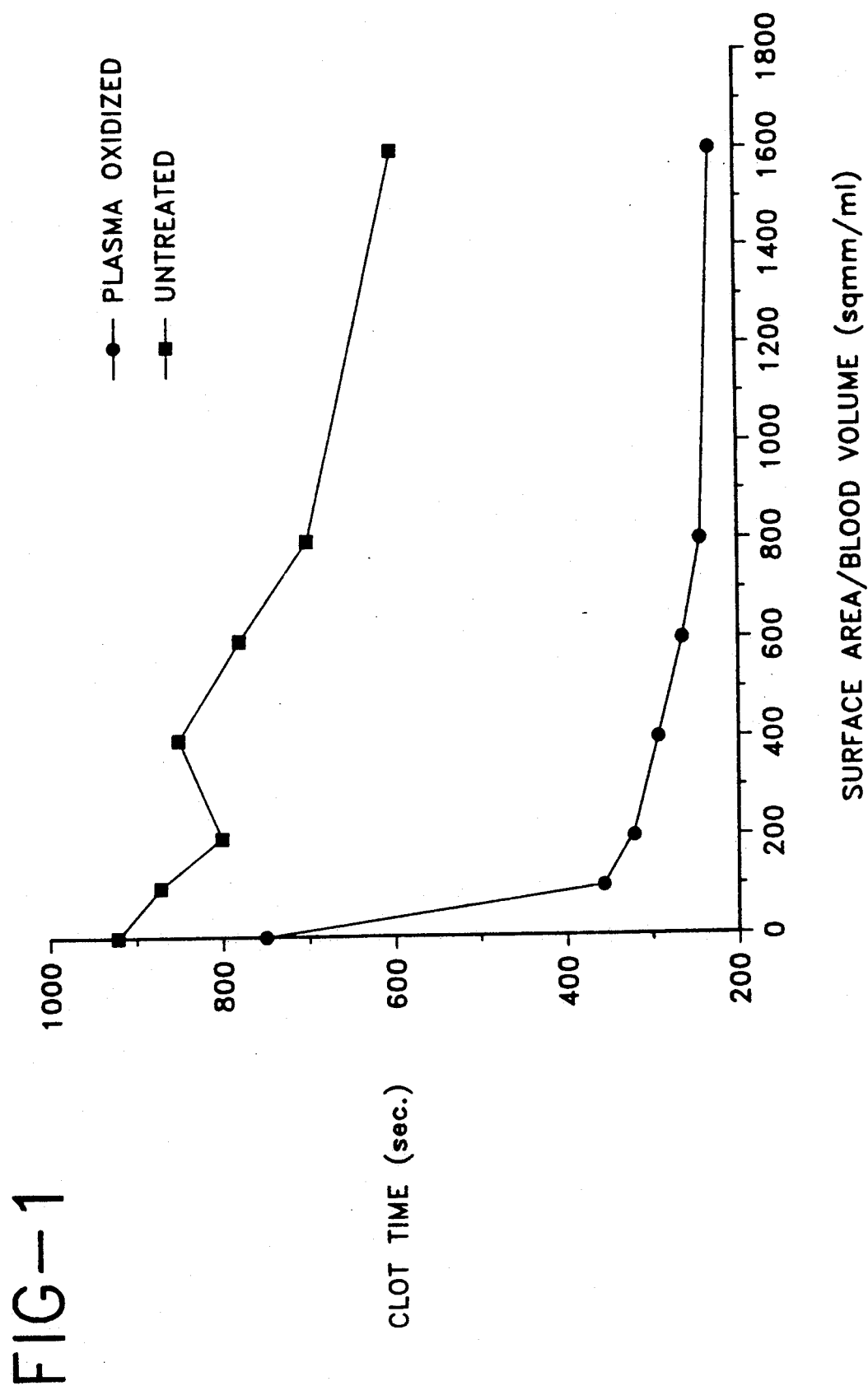
FIG. 1 is a plot showing the relationship between blood clotting time and the ratio of surface area to blood volume of the polystyrene additive of the invention.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

A first aspect of the invention is a blood clotting additive which presents a plurality of surface regions having different surface chemistries to the blood being collected. A first region is highly wettable and initiates clotting but is substantially nonadherent to blood elements along the clotting cascade. The second region is substantially nonwettable and is absorbent to blood proteins so that the developing clot adheres to this region. The additive becomes part of the clot and is trapped in the pellet when the clotted sample is centrifuged.

It will be appreciated that the additive, having a wettable surface region and a nonwettable surface region, may be prepared from any substrate having any original surface chemistry. Thus a substrate which has a wettable original surface chemistry may be modified to produce a second surface region which is substantially nonwettable. Conversely, a substrate which has a substantially nonwettable original surface chemistry may be modified to produce a second surface region which is substantially wettable.

In one embodiment of the invention, metal oxides and mineral silicates, such as aluminum oxide, silicon dioxide, aluminum silicate and glass may be used as the substrate. The surface of these materials, particularly glass, is highly wettable, and can serve as a first surface region. A second surface region may then be rendered nonwettable by any suitable procedure. This embodiment of the invention will be described in detail for the preferred substrate, glass.

The glass may be in any form, such as a plate, bead or disc. While the size of the substrate is not critical, a preferred size is a bead or plate about 1 to 10 mm thick or a disc about 0.1 to 2.0 mm thick. A glass plate or disc may be treated to render one side nonwettable, after which the plate may simply be broken into pieces of various sizes. For treatment of beads, a monolayer of the beads in any suitable container may be treated. Treatment with a silylating agent, such as dichlorodimethylsilane, may be performed to cause silylation of the contacted surface area and render it substantially nonwettable. Silylation of glass is conventional.

Alternatively, a hydrophobic layer may be deposited on a portion of the glass surface. Any deposition method, such as dip coating, may be used. Preferably, gas plasma deposition of a polymeric layer is carried out. One surface area of the glass substrate may be shielded from the gas plasma in any suitable way. For example, a flat plate or disc may be placed on top of a dielectric so that only one surface area is exposed to the gas plasma. For glass beads, the dielectric may have semicircular depressions into which the beads are snugly fit so that only a portion of the bead surface is exposed. The substrate and dielectric may be supported in a conventional plasma chamber and a gas plasma developed from a gas such as hydrogen, fluorine or a hydrocarbon such as methane or hexane. The plasma may be generated using conventional plasma conditions such as DC or AC power levels up to about 200 watts, RF frequency of about 0.1 to 50 megahertz, about 0.1 to 30 minutes, and a gas pressure of about 0.1 to 3.0 Torr respectively. Gas plasma deposition of a polymeric layer is well known and exemplified by Auerbach in U.S. Pat. No. 4,188,426 wherein fluorinated hydrocarbons are plasma polymerized and deposited from carbene intermediates. Selection of plasma parameters is well within the purview of one skilled in the art.

In a preferred embodiment of the invention, the additive is prepared from a polymer having a substantially nonwettable original surface chemistry. Suitable polymers are, for example, polyethylene, polypropylene, polyvinyl chloride and preferably polystyrene. The substantially nonwettable original surface may serve as a first surface chemistry of the additive.

A second region of the surface may then be treated in any way which converts the original nonwettable surface chemistry to a substantially wettable surface. A preferred method to achieve wettability is gas plasma treatment. Thus, for example, the polymer may be cast into a film about 0.1 to 10, preferably about 1 to 4 microns in thickness. The thickness of the film is not critical.

The film may then be placed in the chamber of any conventional plasma generator, after protecting one side from the plasma. For example, the polymeric film may be placed on a dielectric so that only the upward—facing polymeric surface is exposed to the plasma. Most preferably, the film is prepared by casting onto a glass plate, and the plate having the film thereon is placed in the chamber.

Although an RF ionizing plasma is preferred, any other method of generating an ionizing gas plasma may be used, for example a glow discharge or a corona discharge. The plasma may be generated from any process gas or mixture of gases known to give wettable surfaces. Suitable gases are, for example air, ammonia, carbon dioxide, sulfur dioxide, and preferably oxygen. Gas plasma parameters within the ranges given above may be used.

The plasma treated film may be used as a single piece or preferably may be cut into any number of pieces of any desired size to serve as the additive of the invention. The individual pieces may be about 1–50, preferably about 20–40 square mm in area. The pieces of additive may be of any convenient shape. Preferred additives are particles, chips, or flakes and may be square, rectangular or circular.

It will be apparent to one skilled in the art that clotting will be initiated sooner and proceed faster when the blood sample is exposed to a greater area of wettable additive surface. Thus, the greater the number of pieces of additive, the faster the clotting. On the other hand, too many pieces of additive may interfere with the centrifugation and lead to a poorly defined pellet. It has been found that about 10 to 100,000 preferably about 100 to 10,000, most preferably about 300 to 1000 total square mm of wettable surface for each ml of blood may be used. The number of pieces of additive to be used thus may easily be determined by one skilled in the art based on the volume of the blood sample and the total surface area of the pieces of additive.

In accordance with the invention, the terms wettable and nonwettable may be defined by the contact angles made when the two surface regions of the additive are wetted with water. In its broadest scope, the invention contemplates a nonwettable surface having a contact angle of 35° or higher and a wettable surface having a contact angle of 0° to 34°. Preferred nonwettable surfaces have a contact angle of 120° to 45°, most preferably about 100° to 65°. Preferred wettable surfaces have a contact angle of about 0° to 25°, most preferably about 0° to 10°.

Another aspect of the invention is a blood collection assembly which includes the clotting additive of the invention. The assembly may include a container for receiving the blood sample. The preferred container is a tube which may be plastic or preferably glass. In the most preferred assembly of the invention, a glass collection tube having one closed end and the additive therein may be combined with a septum over the open end and evacuated. Evacuated tubes for blood collection are standard in the art, as, for example, VACUTAINER TM brand tubes (Becton, Dickinson and Company).

The following examples are provided to further described the invention but are not to be considered as limitative of the invention.

EXAMPLE I

This experiment illustrates differences in the adherence of fibrin and blood clot materials to native polystyrene and oxidized polystyrene.

A strip of polystyrene film was clamped between two glass plates leaving about half of the film exposed, and the entire assembly exposed to an oxygen plasma generated in a conventional planer diode plasma unit operated at an RF frequency of 13.56 megahertz at a pressure of 200–300 mTorr for 20 seconds. The portion between the glass plates was effectively masked from the oxidative environment and remained in the untreated, nonwettable state while the exposed section was oxidized and became substantially wettable with water. Thus, on the same film surface, the reactivity of the oxidized and unoxidized surface chemistries toward blood could be observed. The film was rolled into a cylinder and inserted into a 5 ml. glass test tube with the boundary between the treated and untreated sides arranged axially in the tube. Whole porcine (pig) blood was added and allowed to clot for 15 minutes, after which the tube was centrifuged in a standard hematological centrifuge and observed visually. The nonwettable side of the boundary line had clot adhering to the surface whereas there was no adherence of the clot to the treated side. The film was removed, washed with buffer and examined under a phase contrast microscope. Micrographs clearly showed adherence of fibrin and blood cells to the untreated portion of the film, with a sharp boundary separating the treated and untreated portions. Little or no fibrin or blood cells were observed to be adherent to the treated, oxidized film. This experiment illustrates that the two surface chemistries exhibit two separate adherent properties in the presence of clotted blood.

EXAMPLE II

This experiment illustrates the clot activating property of surface-oxidized polystyrene film.

Using the glass-plate masking scheme described in Example I, a strip of polystyrene was plasma oxidized with either one or both faces masked. These two sources of film were cut into circles 6 millimeters in diameter using a hole punch to give additive particles with either one or both sides exhibiting the oxidized surface chemistry. Four particles of each kind were added to polystyrene test tubes. A standard amount (0.5 ml.) of platelet poor plasma, obtained by separating cells from plasma by centrifugation of citrated porcine blood, was added to the tubes. The tubes were incubated for 15 minutes at 37° C. after which calcium chloride was added to initiate clotting. Tube contents were then mixed on a laboratory inverting mixer and the time of clotting noted for each test. Table I collects clot time data for 4 replicate experiments, and compares control polystyrene and glass tubes (no additive), and polystyrene tubes having particles of untreated additive, additive particles with one side plasma treated and additive particles with both sides treated.

TABLE I

| | CLOTTING TIMES (SEC.) | | | | |
|---|---|---|---|---|---|
| | WITHOUT ADDITIVE | | WITH ADDITIVE | | |
| | glass control | PS control | untreated | 1 side | 2 sides |
| 1 | 145 | 190 | 192 | 85 | 62 |
| 2 | 124 | 165 | 140 | 85 | 65 |
| 3 | 175 | 220 | 224 | 135 | 100 |
| 4 | 160 | 240 | 225 | 115 | 120 |
| AVE | 151 | 204 | 195 | 105 | 87 |

It is seen from Table I that the oxidative plasma reduces clotting time by a factor of approximately 2 using the dual surface chemistry additive particles. A further reduction in clotting time is noted when the second side of the particles is oxidized.

EXAMPLE III

This experiment illustrates the relationship between oxidized surface area of the polystyrene additive and blood clotting time.

The oxidized polystyrene film of Example II and an untreated polystyrene film were cut into 5 mm square film sections. Tubes containing 1 ml of blood plasma were treated with varying numbers of film sections and the time required to substantially clot the blood was measured. The results of this experiment are shown in FIG. 1. It is seen that, for any given surface area, clotting is greatly enhanced by the oxidized polystyrene surface of the additive.

EXAMPLE IV

This experiment illustrates clotting de-activation by gas plasma coating of glass beads with a polymerized hexane layer.

Figure 2:
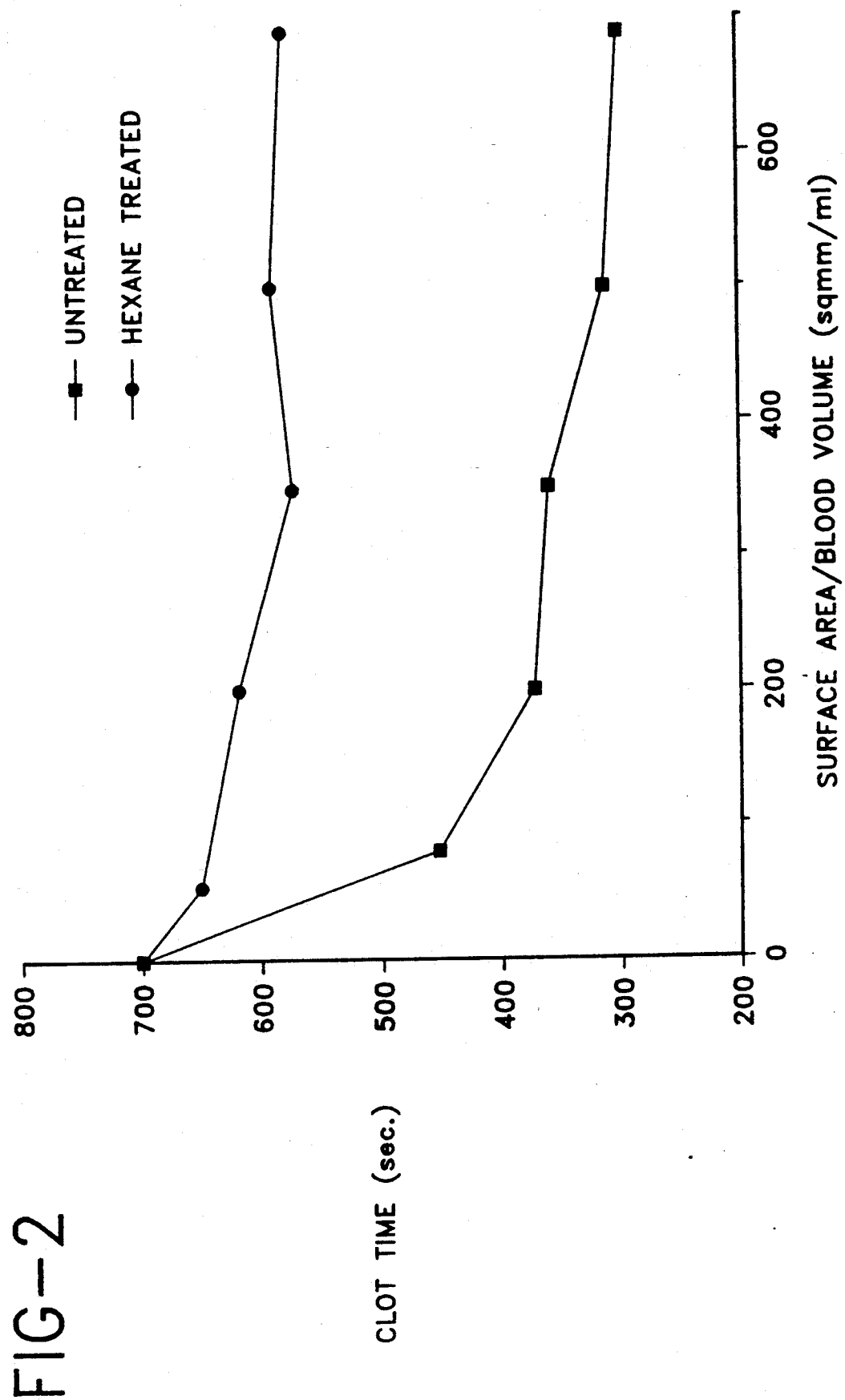
FIG. 2 is a plot showing the relationship between blood clotting time and the ratio of surface area to blood volume of the glass additive of the invention.

Glass beads (0.6 mm diameter) were exposed for 1 minute to a hexane plasma generated in a planer diode plasma unit at 600 mTorr and a frequency of 13.56 megahertz. The beads were assayed for clot activation by the procedure of Example II. The results are shown in FIG. 2 which plots total surface area of beads per ml of blood plasma against the time required for substantial clotting. It is seen that the hexane treated beads were significantly slower than untreated beads in promoting clotting.

EXAMPLE V

The following experiments were performed to verify that dual surface chemistry additive particles become incorporated into a blood clot and cleanly separate from plasma upon certrifugation in a blood tube.

The glass-plate masking technique described in EXAMPLE II was employed to make 6 mm additive particles with a dual surface chemistry. Particles were added to glass test tubes with porcine blood. After the blood had substantially clotted, the tube was centrifuged to separate serum from clot. When inspected visually, no additive particles were observed in the serum layer, but particles were found within the clot and attached to the fibrin/cell mass.

EXAMPLE VI

In the same way as described in Example IV, 12 mm diameter glass cover slips were plasma treated with hexane to deposit a hexane layer on one side only of the slips. In the same way as described in Example V, these dual action slips were added to porcine blood in glass test tubes. After clotting was complete and the tubes centrifuged, the clots were examined visually. The cover slips were easily seen to be occluded in the clot material. No cover slips were free in the serum layer.

What is claimed is:

1. An additive for a blood collection container comprising a substrate having a first surface region which is substantially wettable by blood serum and a second surface region which is substantially nonwettable by blood serum, said first region activating clotting of blood but being nonadherent to blood clotting materials and said second region being adherent to said blood clotting materials so that, when a blood sample in said container is centrifuged, said additive becomes part of a clot and is removed from a serum layer.

2. An additive for a blood collection container comprising a substrate having a first surface region having a wettability towards blood serum defined by a contact angle of 35° or less and a second surface region having a wettability towards blood serum defined by a contact angle of more than 35°, said first region activating clotting of blood but being nonadherent to blood clotting materials and said second region being adherent to said blood clotting materials so that, when a blood sample in said container is centrifuged, said additive becomes part of a clot and is removed from a serum layer.

3. The additive of claim 2 wherein said substrate is glass.

4. The additive of claim 3 wherein said first region is a coating on said glass.

5. The additive of claim 4 wherein said coating is a silane coating.

6. The additive of claim 4 wherein said coating is a polymeric coating.

7. The additive of claim 6 wherein said polymeric coating is plasma-deposited hexane.

8. The additive of claim 2 wherein said substrate is a polymer.

9. The additive of claim 8 wherein said polymer is selected from the group consisting of polystyrene, polypropylene and polyvinyl chloride.

10. The additive of claim 8 wherein said first region has been generated with a wettability-generating plasma.

11. The additive of claim 10 wherein said plasma is generated from a process gas selected from the group consisting of air, oxygen, nitrogen, carbon dioxide and sulfur dioxide.

12. An additive for a blood collection container comprising a glass particle, said particle having a first side charactertized by a contact angle of about 0° to 25 and a second side characterized by a contact angle of 120 to 45°, said first side activating clotting of blood but being nonadherent to blood clotting materials and said second side being adherent to said blood clotting materials so that, when a blood sample in said container is centrifuged, said additive becomes part of a clot and is removed from a serum layer.

13. A blood collection assembly comprising a blood collection container having an open end and a closed end, said container having therein the additive of claim 1.

14. The assembly of claim 13 further comprising a puncturable septum over said open end of said blood collection container.

15. The assembly of claim 14 wherein said container is evacuated.

16. A blood collection assembly comprising a blood collection container having an open end and a closed end, said container having therein the additive of claim 2.

17. The assembly of claim 16 further comprising a puncturable septum over said open end of said blood collection container.

18. The assembly of claim 17 wherein said container is evacuated.

19. A blood collection assembly comprising a blood collection container having an open end and a closed end, said container having therein the additive of claim 12.

20. The assembly of claim 19 further comprising a puncturable septum over said open end of said blood collection container.

21. The assembly of claim 20 wherein said container is evacuated.

* * * * *